US00PP30844P2

(12) United States Plant Patent
Meilland

(10) Patent No.: US PP30,844 P2
(45) Date of Patent: Aug. 27, 2019

(54) BEDDING ROSE PLANT NAMED 'MEIRYEZZA'

(50) Latin Name: *Rosa hybrida*
Varietal Denomination: MEIRYEZZA

(71) Applicant: THE CONARD-PYLE COMPANY, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,709

(22) Filed: Apr. 12, 2018

(51) Int. Cl.
*A01H 5/02* (2018.01)
*A01H 6/74* (2018.01)

(52) U.S. Cl.
USPC ..... Plt./102
CPC ..... *A01H 6/74* (2018.05)

(58) Field of Classification Search
USPC ..... Plt./107, 102
CPC ..... A01H 5/0222
See application file for complete search history.

(56) References Cited

U.S. PATENT DOCUMENTS

PP7,785 P 2/1992 Meilland
PP16,202 P2 1/2006 Radler

*Primary Examiner* — Kent L Bell
(74) *Attorney, Agent, or Firm* — Buchanan Ingersoll & Rooney PC

(57) ABSTRACT

A new and distinct variety of Bedding Rose plant, herein referred to by its cultivar name, 'MEIRYEZZA', is provided which forms very abundantly on a nearly continuous basis attractive, cup-shaped, cream colored blossoms margined with a bright red-purple coloration. Attractive, glossy, dense foliage is formed, which contrasts beautifully with the blossoms. A compact, bushy growth habit is displayed. The disease tolerance is good, particularly against rust. The new variety is well suited for proving attractive ornamentation in the landscape.

1 Drawing Sheet

Botanical/commercial classification: Latin name—*Rosa hybrida.* Common name—Bedding Rose Plant. Varietal denomination—'MEIRYEZZA'.

SUMMARY OF THE INVENTION

The new variety of *Rosa hybrida* Bedding Rose plant was created by artificial pollination wherein two parents were crossed which previously had been studied in the hope that they would contribute the desired characteristics. The female parent (i.e., the seed parent) was the product of the cross of the 'MEICHOIJU' variety (non-patented in the United States) and the 'MEIKIJI' variety (U.S. Plant Pat. No. 7,785). The male parent (i.e., the pollen parent) was the 'RADTKO' variety (U.S. Plant Pat. No. 16,202).

The parentage of the new variety can be summarized as follows:

('MEICHOIJU' x 'MEIKIJI') x 'RADTKO'

The seeds resulting from the above pollination were sown and small plants were obtained which were physically and biologically different from each other. Selective study resulted in the identification of a single plant of the new variety.

It was found that the new variety of Bedding Rose plant of the present invention possesses the following combination of characteristics:

(a) very abundantly and nearly continuously forms attractive, cup-shaped, cream colored blossoms margined with a bright red-purple coloration,
(b) forms attractive, dense, glossy foliage, (c) exhibits good tolerance to diseases, particularly against rust,
(d) displays a compact, bushy growth habit, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEICHOIJU' variety (i.e., parent of the seed parent) displays pink colored blossoms and the 'RADTKO' variety (i.e., the pollen parent) displays red colored blossoms, whereas the new variety displays cream colored blossoms margined with bright red-purple coloration. The 'MEIKIJI' variety (i.e., parent of the seed parent) display flowers possessing approximately 25 to 30 petals on average, while the new variety displays flowers possessing approximately 34 to 39 petals on average. In addition, the female parent, the ('MEICHOIJU' x 'MEIKIJI') variety, (i.e., the seed parent) exhibits larger flowers and a more upright plant habit compared to the new variety.

Moreover, the new variety can be readily distinguished from other similar non-parental varieties. For example, the 'MEIZYGGLIE' variety (U.S. Plant patent application Ser. No. 15/932,688, filed on Apr. 10, 2018, Pending) displays red colored blossoms, whereas the new variety provides cream colored blossoms margined with a bright red-purple coloration.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEIRYEZZA'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plant of the new variety was approximately two years of age and was observed during November while budded on its own roots and growing outdoors at Le Cannet des Maures, Var, France.

FIG. 1—illustrates a specimen of a plant displaying foliage and multiple flowers, including three flowers in the course of opening—plan view—obverse.

DETAILED BOTANICAL DESCRIPTION

The chart used in the identification of the colors is that of The Royal Horticultural Society (R.H.S. Colour Chart), London, England. The terminology which precedes reference to the chart has been added to indicate the corresponding color in more common terms. The description is based on the observation of two-year-old specimens of the new variety during November while budded on their own roots and growing outdoors at Le Cannet des Maures, Var, France.

Class: Bedding Rose Plant.

Plant:

*Habit*.—Compact, bushy.

*Height*.—Typically between 60 cm and 65 cm.

*Diameter*.—Approximately 50 cm on average.

Branches:

*Size*.—Length: typically 40 cm to 50 cm. Diameter: typically 0.6 cm to 1.0 cm.

*Color*.—Young stems: commonly near Yellow-Green Group 147C. Adult wood: commonly near Yellow-Green Group 146A.

*Thorns*.—Configuration on adult stems: very elongated on the upper surface and slightly concave on the under surface. Long prickles (≥0.6 cm) — quantity: commonly approximately 4 thorns per 10 cm long young stem and commonly 7 thorns per 10 cm long adult stem. Long prickles (≥0.6 cm) — base shape: oval. Long prickles (≥0.6 cm) — size: commonly near 0.6 cm in length on average on young stems and commonly near 1.0 cm in length on average on adult stems. Long prickles (≥0.6 cm) — color: commonly near Greyed-Yellow Group 162C on young stems and commonly near Greyed-Orange Group 164A on adult stems. Small prickles (<0.6 cm) — none observed.

Foliage:

*General appearance*.—Dense with a glossy aspect.

*Number of leaflets*.—3, 5, and 7; most often 5 or 7.

*Terminal leaflet*.—Length: approximately 5.2 cm on average. Width: approximately 3.7 cm on average.

*New foliage*.—Upper surface color: commonly near Yellow-Green Group 146B. Under surface color: commonly near Yellow-Green Group 146C.

*Adult foliage*.—Upper surface color: commonly near Yellow-Green Group 147A. Under surface color: commonly near Yellow-Green Group 147B.

*Entire leaf*.—Length: typically 9.0 to 12 cm on average. Width: typically 6.0 to 8.5 cm on average.

Leaflets:

*Shape*.—Tip: rounded. Base: obtuse.

*Texture*.—Leathery.

*General appearance*.—Oval.

*Edge*.—Slightly denticulate.

*Serration*.—Small and single.

*Petiole rachis*.—Length: typically between 2.5 cm to 5.5 cm. Diameter: typically between 0.1 cm to 0.2 cm. Color of upper surface: commonly near Green Group 138C. Color of under surface: commonly near Green Group 138B.

*Petioles*.—Upper surface: no glandular. Under surface: many prickles. Color of upper surface: commonly near Yellow-Green Group 148C. Color of under surface: commonly near Yellow-Green Group 148B. Length: typically 2.5 cm to 3.5 cm. Diameter: typically 0.1 cm to 0.2 cm. Petiole length of terminal leaflet: commonly near 3.0 cm on average. Petiole diameter of terminal leaflet: approximately 0.1 cm on average.

*Stipules*.—General appearance: adnate, pectinate and rather broad. Length: approximately 1.7 cm on average. Width: approximately 0.5 cm on average. Color of upper surface: commonly near Green Group 138B. Color of under surface: commonly near Green Group 138B.

Inflorescence:

*Number of flowers per stem*.—Generally between 1 and 5 flowers per stem.

*Lastingness of the bloom*.—Typically between 8 to 10 days.

*Bud*.—Shape: conical. Size: medium. Length: approximately 2.0 cm on average. Width: approximately 1.7 cm on average. Color as calyx breaks: Upper surface: internal petals are commonly near Yellow-White Group 158B; external petals are commonly near Yellow-White Group 158B margined with near Red-Purple Group 57A. Under surface: commonly near Yellow-White Group 158B.

*Sepals*.—Number commonly 5. Length: approximately 1.9 cm on average. Width: approximately near 0.6 cm on average. Shape: some elongated extensions (approximately 1.2 cm on average), at the top: narrow and longish, at the base: upright. Upper surface: Texture: tomentous. Color: commonly near Green Group 138C. Under surface: Texture: smooth. Color: commonly near Green Group 138B.

*Receptacle*.—Color: commonly near Green Group 138B. Length: approximately 0.7 cm on average. Width: approximately 0.7 cm on average. Surface: smooth. Shape: funnel shaped.

*Peduncle*.—Length: approximately 4.0 cm on average. Width: approximately 0.2 cm on average. Surface: glandular. Color: commonly near Green Group 138B.

*Flower*.—Average diameter when fully open: approximately 8.0 cm on average. Depth: commonly near 5.0 cm on average. Borne: commonly between 1 to 5 flowers per stem. Shape: cup shaped. Number of petals under normal conditions: approximately 34 to 39 petals on average. Shape of the petal: sometimes cordiform and slightly undulated. Base: obtuse. Top: rounded. Texture of the petal: leathery. Petal length: approximately 3.5 cm on average. Petal width: approximately 3.0 cm on average. Petal arrangement: imbricated without petaloids. Petal drop: petals drop off cleanly before drying. Fragrance: none. Color when opening: Upper surface: internal petals are commonly near Yellow-White Group 158B to 158C; external petals are commonly near Yellow-White Group 158B to 158C more or less margined with near Red-Purple Group 57B. Under surface: internal petals are commonly near Yellow-White Group 158B to 158C; external petals are commonly near Yellow-White Group 158B to 158C more or less suffused with near Red-Purple Group 63B and margined with near Red-Purple Group 57B. Color of the open flower: Upper surface: internal petals are commonly near Yellow-White Group 158B to 158C; external petals are commonly near Yellow-White Group 158B to 158C more or less margined with near Red-Purple Group 57B. Under surface: internal petals are commonly near Yellow-White Group 158B to 158C; external petals are commonly near Yellow-White Group 158B to 158C more or less suffused with near Red-Purple Group 63B and margined with near Red-Purple Group 57B. Anthers: number is approximately 57 on average, length is approximately 0.1 cm on average, coloration is commonly near Yellow Group 8C, and arrangement is regular around styles. Filaments: length is approximately 0.4 cm on average and coloration is commonly near Greyed-Yellow Group 162D. Styles: length is approximately 0.3 cm on average, coloration is commonly near Red Group 45C, and number is approximately 53 on average. Stigmas: size is approximately 0.1 cm on average and coloration is commonly near Yellow Group 2D. Pollen: not available at this stage. Hips: not available at this stage.

Development:

*Vegetation*.—Strong.

*Blooming*.—Early in the season, typically May to November, very abundant and nearly continuous.

*Tolerance to disease*.—Good, and particularly against rust.

The new 'MEIRYEZZA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Bedding Rose plant characterized by the following combination of characteristics:

(a) very abundantly and nearly continuously forms attractive, cup-shaped, cream colored blossoms margined with a bright red-purple coloration, (b) forms attractive, dense, glossy foliage, (c) exhibits good tolerance to diseases, particularly against rust, (d) displays a compact, bushy growth habit, and (e) is well suited for providing attractive ornamentation; substantially as herein shown and described.

* * * * *

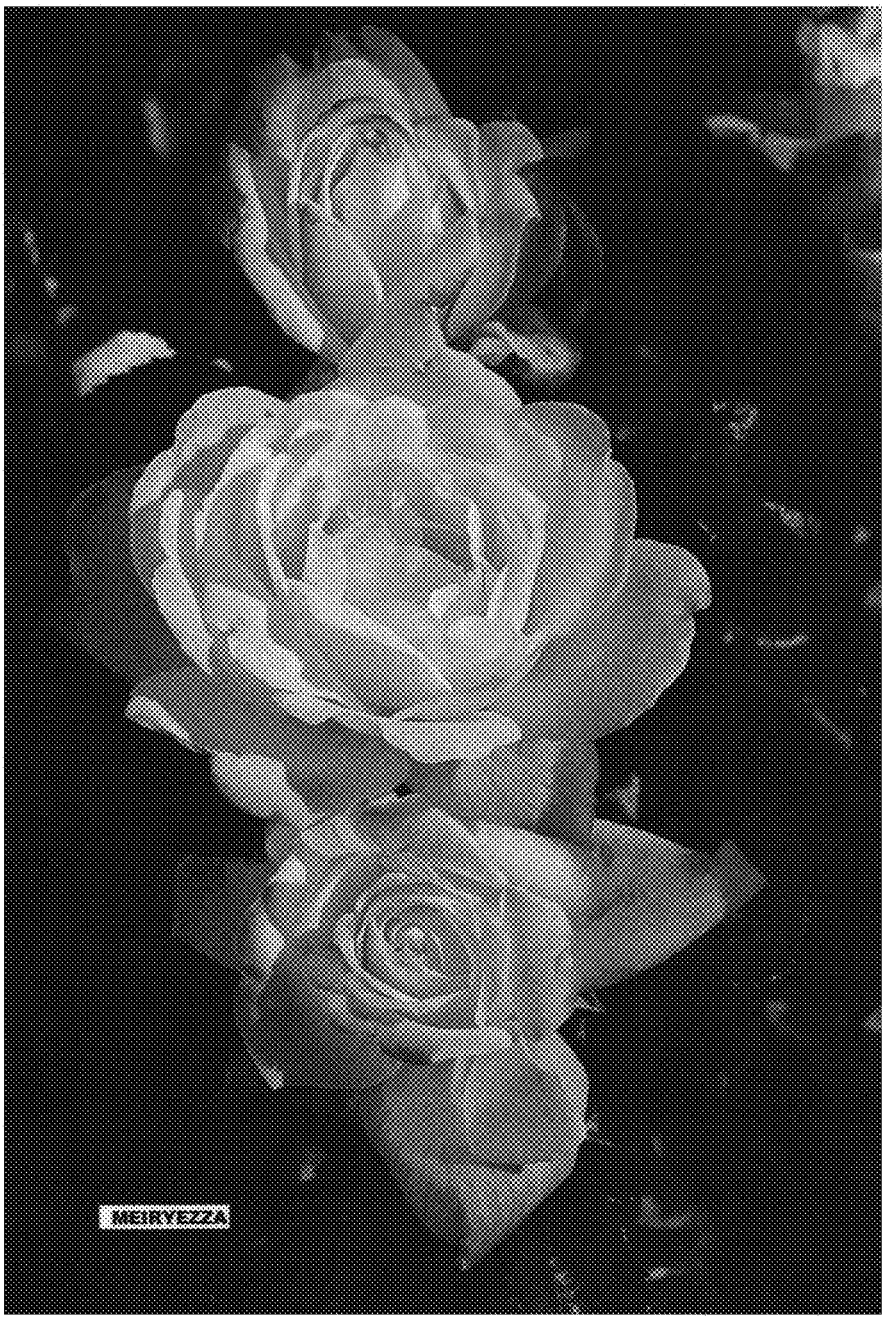
MEIRYEZZA